United States Patent [19]

Bradford

[11] Patent Number: Plant 5,663

[45] Date of Patent: Feb. 18, 1986

[54] NECTARINE TREE (JULY RED)

[76] Inventor: Norman G. Bradford, 11875 E. Savana Rd., Le Grand, Calif. 95333

[21] Appl. No.: 622,086

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

The present invention relates to a nectarine tree and more particularly to a new and distinct variety broadly characterized by a large, vigorous, hardy, very productive and regular bearing tree. The fruit is a clingstone, and under the ecological conditions described, ripens about three days later than Red Grand (U.S. Plant Pat. No. 1,060), and is firmer and larger. The fruit also has a bright, almost solid red skin color, an attractive globose form, and is of very good eating quality.

1 Drawing Figure

BACKGROUND OF THE VARIETY

The instant variety was propagated by me at Bradford Farms at Le Grand (San Joaquin Valley), Calif., from the cross of two unnamed seedlings. The seed parent was a Red Free nectarine (U.S. Plant Pat. No. 3,385) by Autumn Gold (U.S. Plant Pat. No. 3,478), and the pollen parent was an open pollinated Red Diamond nectarine (U.S. Plant Pat. No. 3,165). I asexually reproduced the resulting plant by budding and grafting, and such reproduction of plant and fruit characteristics was true to the original plant in all respects.

The instant variety most nearly resembles Red Grand but is distinguished therefrom in that the fruit ripens approximately three days later and is an improvement thereon in having fruit which is larger and has a brighter, almost solid red color, a more attractive, globose form, and firmer flesh. Also, the tree is regular bearing, vigorous and more productive.

The parent plant which this variety most resembles is Red Diamond, as it possesses the Red Diamond firmness and color, but it ripens approximately 30 days later, is a clingstone instead of freestone, and is globose in shape instead of slightly oblong. It differs from the Red Free variety by having fruit which is much firmer, larger in size, clingstone instead of freestone, and ripens approximately five days later. It is similar to Autumn Gold in size and by the fact that both are clingstones, but it ripens approximately 30 days earlier than Autumn Gold and has more glossy, red color.

DRAWINGS

The accompanying photograph shows the characteristics of the whole fruit in skin color and form, of a fruit divided on its suture plane showing the flesh and stone cavity, and a characteristic stone and leaves.

POMOLOGICAL CHARACTERISTICS

Referring now more specifically to the pomological characteristics of this new and distinct variety of nectarine tree, the following has been observed under the ecological conditions prevailing near Le Grand, Merced County, Calif., and was developed at the state of eating ripeness on Aug. 1, 1983. All color plate identifications are by reference to Dictionary of Color 1950 (2nd ed) by Maerz and Paul.

TREE

General: Large, vigorous, hardy, dense and spreading to vase shape. Very productive and regular bearing.

Trunk: Of medium size, shaggy, resembling 15 C-9 in color. Has average number of large, 15 H-12 color lenticles averaging 3/16" to ⅛" in length.

Branches: Stocky, medium smooth, resembling Soapstone (15 A-7) in color on both dorsal and ventral side; medium number of small lenticles.

LEAVES

Size: Medium size, 5½" in length, 1⅜" in width.

Form: Elliptical.

Base: Acute.

Apex: Acuminate.

Margin: Crenate.

Venation: Pinately net veined.

Petiole: Medium; average length ⅜"; medium thickness.

Glands: Averaging two oppositely disposed, medium size, reniform, green glands on the petiole or base of blade.

Stipules: A few, 1/16" in length.

Color: Dorsal side color 22 L-6, ventral side color 22 L-3.

FLOWERS

Buds: Hardy, medium size, medium length; conical, plump, free and pubescent.

Flowers: Medium blooming date compared with other varieties; large, pink.

FRUIT

Maturity when described: Eating ripe on Aug. 10, 1983.

Size: Uniformly large; axial diameter 2⅛", transverse in suture plane, 2⅜".

Form: Globose overall.

Suture: Shallow suture extending from base to apex, with marked depression beyond pistil point.

Ventral surface: Rounded, slightly lipped toward apex on both sides with equal lips.

Cavity: Circular; depth ½", breadth, ⅛". Suture showing on one side.

Base: Rounded.

Apex: Short, rounded.

Pistil point: An inconspicuous speck depressed in the suture.

Stem: Medium: ¾" in length, 3/16" in width.

Skin: Medium thickness, medium texture. Tenacious to the flesh. Only slight tendency to crack.

*Color.*—Resembling Chalet Red (6 K-10).

Flesh:

*Amygdalin.*—Scarce.

*Juice.*—Abundant, rich.

*Texture.*—Medium and melting.

*Fibres.*—Abundant, coarse and tender.

*Ripens.*—Evenly.

*Flavor.*—Subacid.

*Aroma.*—Very slight.

*Eating quality.*—Very good.

*Color of pit cavity.*—Resembling Chimney Red (5 L-10).

*Flesh color.*—Yellow (10 I-7).

STONE

Type: Clingstone.

Form: Oblong, base straight.

Hilum: Narrow and oblong.

Apex: Mucronate, sides equal and flattened.

Surface: Irregularly furrowed throughout.

Apex: Pitted from base to midpoint.

Ridges: Rounded.

Color of stone: Brown resembling (8 H-12).

Thickness of pit wall: $\frac{1}{4}''$.

Tendency to split: Slight.

Kernel: Sweet, viable; oval form; width $\frac{1}{2}''$, length $\frac{3}{4}''$; light yellow pellicle; scant amygdalin.

USE

For market and long distance shipping; good shipping and keeping quality. No unusual susceptibilities to insects or disease have been noted.

I Claim:

1. A new and distinct variety of clingstone nectarine tree, substantially as illustrated and described, which most closely resembles Red Grand (U.S. Plant Pat. No. 1,060) nectarine but is distinguished therefrom and an improvement thereon in that it produces very heavy crops of fruit that ripen three to five days later, is larger and firmer, has a globose form, and a sweet kernel.

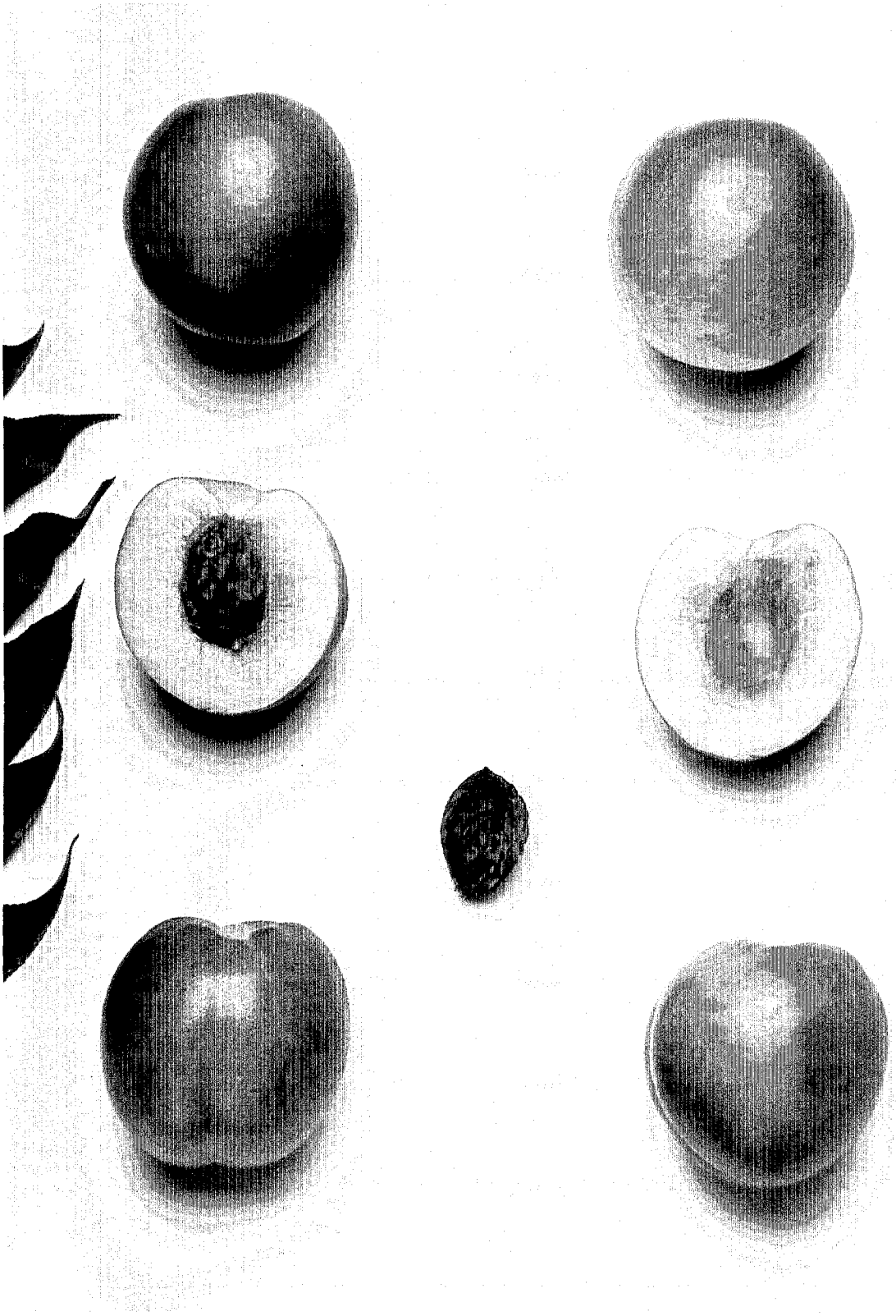

* * * * *